United States Patent [19]

Arai et al.

[11] Patent Number: 5,177,223
[45] Date of Patent: Jan. 5, 1993

[54] INDOLEACETIC ACID DERIVATIVES, PROCESS FOR THEIR PREPARATION, AND MEDICINES CONTAINING SAME AS ACTIVE INGREDIENTS

[75] Inventors: Heihachiro Arai, Konan; Ikuo Ueda, Toyonaka, both of Japan

[73] Assignee: Zeria Pharmaceutical Co., Ltd., Tokyo, Japan

[21] Appl. No.: 465,241

[22] PCT Filed: Jul. 4, 1989

[86] PCT No.: PCT/JP89/00669

§ 371 Date: Apr. 24, 1990

§ 102(e) Date: Apr. 24, 1990

[87] PCT Pub. No.: WO90/00545

PCT Pub. Date: Jan. 25, 1990

[30] Foreign Application Priority Data

Jul. 5, 1988 [JP] Japan ................. 63-165823

[51] Int. Cl.⁵ ............... C07D 403/12; C07D 401/12; A61K 31/41; A61K 31/445
[52] U.S. Cl. ................. 548/500; 546/201; 548/501
[58] Field of Search ......... 548/500, 501; 546/201; 514/323, 419

[56] References Cited

FOREIGN PATENT DOCUMENTS 0000741 2/1979 European Pat. Off.
2281755 3/1976 France
49-27190 7/1974 Japan
51-47708 12/1976 Japan
58-164570 9/1983 Japan

*Primary Examiner*—David B. Springer
*Attorney, Agent, or Firm*—Oblon, Spivak, McClelland, Maier & Neustadt

[57] ABSTRACT

The present invention relates to an indoleacetic acid derivative and a salt thereof expressed by the following formula (I):

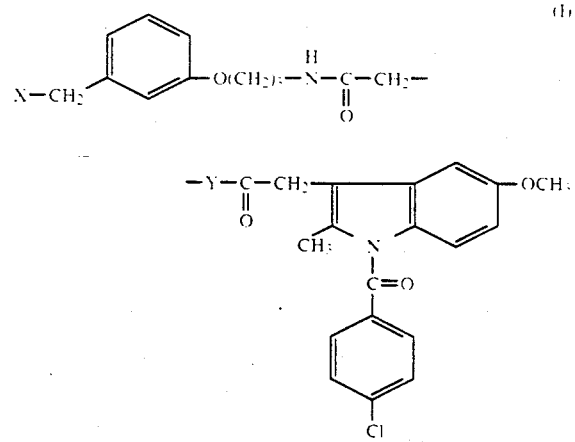

[wherein X denotes a piperidino group, 1-pyrrolidinyl group or 3-hydroxy-1-pyrrolidinyl group; Y denotes

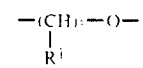

(wherein $R^1$ denotes a hydrogen atom or a lower alkyl group, and l denotes 0, 1 2) or

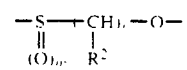

(wherein $R^2$ denotes a hydrogen atom, a lower alkyl group or a hydroxyl group, m denotes 0, 1 or 2, and n denotes 1, 2 or 3)]. The present invention also relates to anti-inflammatory drugs, anti-rheumatic drugs and anti-ulcer drugs containing the above compounds as active ingredients. The compounds possess a strong antiinflammatory action while causing extremely reduced troubles of digestive organs which is a serious defect with conventional non-steroidal anti-inflammatory drugs, and possess an excellent anti-ulcer action as well.

5 Claims, No Drawings

INDOLEACETIC ACID DERIVATIVES, PROCESS FOR THEIR PREPARATION, AND MEDICINES CONTAINING SAME AS ACTIVE INGREDIENTS

DESCRIPTION

1. Technical Field

The present invention relates to an indoleacetic acid derivative which has an anti-inflammatory action, an antirheumatic action and an anti-ulcer action, and particularly to an indoleacetic acid derivative and a salt thereof which have a reduced adverse effect than that of conventional non-steroidal anti-inflammatory drugs, a method of preparing them and an anti-inflammatory drug, antirheumatic drug and anti-ulcer drug each of which contains one of them as an active ingredient.

2. Background Art

Anti-inflammatory drugs are classified into steroid hormones, non-steroidal anti-inflammatory drugs, anti-phlogistic enzymes and immunosuppression agents. Of these drugs, non-steroidal anti-inflammatory drugs are most important drugs and, in recent, they have been actively developed all over the world. However, such non-steroidal anti-inflammatory drugs have many problems in the clinical field. The most critical problem is adverse effects such as damages to the digestive organs and the kidneys. Indomethacin, which is a typical indoleacetic acid-type compound having the strongest anti-inflammatory action among non-steroidal anti-inflammatory drugs, is a first choice drug as a remedy for rheumatism. Although indomethacin has a great curative effect, it has adverse effects such as injuries to the gastrointestine and the kidneys and thus has a critical problem in use. Such adverse effects are serious since indomethacin must be continuously administered to the rheumatics for a long period and a large amount of indomethacin must be used as an anti-inflammatory drug. As this type of anti-inflammatory drugs manifest curative effects and adverse effects which are much different depending upon patients, it is necessary to use various types of drugs.

There is thus demand for an anti-inflammatory drug which has reduced adverse effects such as injuries to the gastrointestine and the kidneys and which is effective with excellent persistence.

On the other hand, a group of anticholinergic drugs and histamine H2 receptor blockers such as Cimetidine are generally used as drugs effective for controlling the gastric-acid secretion in the clinical field.

Anticholinergic drugs have adverse effects of controlling the gastric excretory movement and controlling the thirs, mydriasis and sudation, and also have a limit to the use for inhibiting the aggravation of ulcer and preventing the recurrence thereof even if the drugs are used in amounts which allow the gastric-acid secretion to be substantially inhibited. Cimetidine exhibits adverse effects such as an undesirable central action and an antiandrogen action, and particularly has a problem with respect to the lowering in defensive factors in gastric mucosa, which is observed in curing treatment for a long period. It is said that this mainly causes the recurrence of ulcer after the use of cimetidine has been stopped.

There has been arisen a demand for a compound capable of effectively controlling the secretion of the gastric acid serving as an aggressive factor, capable of reinforcing the defensive factor (cytoprotection action) and also having an excellent anti-ulcer action.

Considering the above-mentioned situation, the inventors energetically researched with a view to developing an excellent anti-inflammatory drug, antirheumatic drug, and anti-ulcerative drug. As a result, the inventors found that novel indoleacetic acid derivatives expressed by the formula (I) below and salts thereof have an excellent anti-inflammatory action, antirheumatic action and anti-ulcer action and exhibit extremely reduced adverse effects. This led to the achievement of the present invention.

DISCLOSURE OF INVENTION

The present invention provides indoleacetic acid derivatives expressed by the following formula (I) and salts thereof:

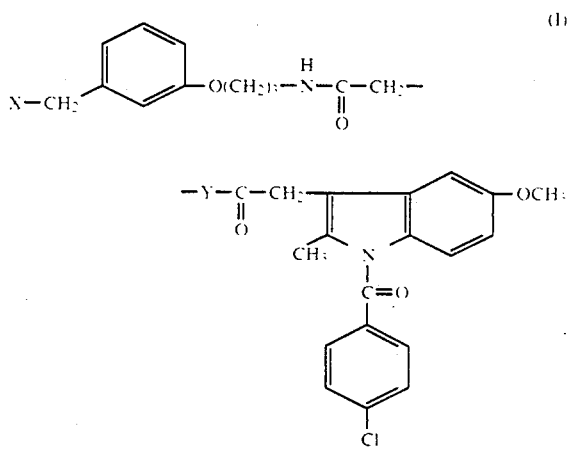

[wherein X denotes a piperidino group, 1-pyrrolidinyl group or 3-hydroxy-1-pyrrolidinyl group; Y denotes

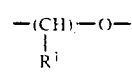

(wherein $R^1$ denotes a hydrogen atom or a lower alkyl group, l denotes 0, 1 or 2) or

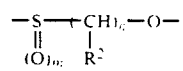

(wherein $R^2$ denotes a hydrogen atom, a lower alkyl group or a hydroxyl group; m denotes 0, 1 or 2; and n denotes 1, 2, or 3)]. The present invention also provides a method of producing these compounds and an anti-inflammatory drug, anti-rheumatic drug and anti-ulcerative drug each of which contains as an active ingredient one of the compounds.

In the compounds (I) of the present invention, examples of lower alkyl groups include straight chain, branched chain or cyclic alkyl groups each having 1 to 6 carbon atoms such as methyl, ethyl, n-propyl, isopropyl, cyclopropyl, n-butyl, isobutyl, 1-methylpropyl, tert-butyl, cyclopropylmethyl, n-pentyl, cyclopentyl, n-hexyl, cyclohexyl and the like.

Examples of salts of the compounds (I) of the present invention include salts, which are physiologically allowable, for example, inorganic acid salts such as hydrochlorides, sulfates, nitrates, and the like; and organic acid salts such as acetates, oxalates, tartrates, malates, citrates, maleates, fumarates and the like.

Typical examples of the compounds (1) of the present invention include the following:

N-[3-[3-(piperidinomethyl)phenoxy]propyl]carbamoylmethyl 1-(4-chlorobenzoyl)-5-methoxy-2-methyl-3-indolylacetate N-[3-[3-(1-pyrrolidinylmethyl)phenoxy]propyl]carbamoylmethyl 1-(4-chlorobenzoyl)-5-methoxy-2-methyl-3-indolylacetate N-[3-[3-(3-hydroxy-1-pyrrolidinylmethyl)phenoxy]propyl]carbamoylmethyl 1-(4-chlorobenzoyl)-5-methoxy-2-methyl-3-indolylacetate 2-[N-[3-[3-(piperidinomethyl)phenoxy]propyl]carbamoyl]ethyl 1-(4-chlorobenzoyl)-5-methoxy-2-methyl-3-indolylacetate 2-[N-[3-[3-(1-pyrrolidinylmethyl)phenoxy]propyl]carbamoyl]ethyl 1-(4-chlorobenzoyl)-5-methoxy-2-methyl-3-indolylacetate 2-[N-[3-[3-(3-hydroxy-1-pyrrolidinylmethyl)phenoxy]propyl]carbamoyl]ethyl 1-(4-chlorobenzoyl)-5-methoxy-2-methyl-3-indolylacetate 1-methyl-2-[N-[3-[3-(piperidinomethyl)phenoxy]propyl]carbamoyl]ethyl 1-(4-chlorobenzoyl)-5-methoxy-2-methyl-3-indolylacetate 1-methyl-2-[N-[3-[3-(1-pyrrolidinylmethyl)phenoxy]propyl]carbamoyl]ethyl 1-(4-chlorobenzoyl)-5-methoxy-2-methyl-3-indolylacetate 3-[N-[3-[3-(piperidinomethyl)phenoxy]propyl]carbamoyl]propyl 1-(4-chlorobenzoyl)-5-methoxy-2-methyl-3-indolylacetate 3-[N-[3-[3-(1-pyrrolidinylmethyl)phenoxy]propyl]carbamoyl]propyl 1-(4-chlorobenzoyl)-5-methoxy-2-methyl-3-indolylacetate 2-[N-[3-[3-(piperidinomethyl)phenoxy]propyl]carbamoylmethylthio]ethyl 1-(4-chlorobenzoyl)-5-methoxy-2-methyl-3-indolylacetate 2-[N-[3-[3-(1-pyrrolidinylmethyl)phenoxy]propyl]carbamoylmethylthio]ethyl 1-(4-chlorobenzoyl)-5-methoxy-2-methyl-3-indolylacetate 2-[N-[3-[3-(3-hydroxy-1-pyrrolidinylmethyl)phenoxy]propyl]carbamoylmethylthio]ethyl 1-(4-chlorobenzoyl)-5-methoxy-2-methyl-3-indolylacetate 2-[N-[3-[3-(piperidinomethyl)phenoxy]propyl]carbamoylmethylsulfinyl]ethyl 1-(4-chlorobenzoyl)-5-methoxy-2-methyl-3-indolylacetate 2-[N-[3-[3-(1-pyrrolidinylmethyl)phenoxy]propyl]carbamoylmethylsulfinyl]ethyl 1-(4-chlorobenzoyl)-5-methoxy-2-methyl-3-indolylacetate 2-[N-[3-[3-(piperdinomethyl)phenoxy]propyl]carbamoylmethylsulfonyl]ethyl 1-(4-chlorobenzoyl)-5-methoxy-2-methyl-3-indolylacetate 2-[N-[3-[3-(1-pyrrolidinylmethyl)phenoxy]propyl]carbamoylmethylsulfonyl]ethyl 1-(4-chlorobenzoyl)-5-methoxy-2-methyl-3-indolylacetate 2-[N-[3-[3-(3-hydroxy-1-pyrrolidinylmethyl)phenoxy]propyl]carbamoylmethylsulfonyl]ethyl 1-(4-chlorobenzoyl)-5-methoxy-2-methyl-3-indolylacetate 1-methyl-2-[N-[3-[3-(piperidinomethyl)phenoxy]propyl]carbamoylmethylthio]ethyl 1-(4-chlorobenzoyl)-5-methoxy-2-methyl-3-indolylacetate 1-methyl-2-[N-[3-[3-(1-pyrrolidinylmethyl)phenoxy]propyl]carbamoylmethylthio]ethyl 1-(4-chlorobenzoyl)-5-methoxy-2-methyl-3-indolylacetate 1-methyl-2-[N-[3-[3-(3-hydroxy-1-pyrrolidinylmethyl)phenoxy]propyl]carbamoylmethylthio]ethyl 1-(4-chlorobenzoyl)-5-methoxy-2-methyl-3-indolylacetate 1-methyl-2-[N-[3-[3-(piperidinomethyl)phenoxy]propyl]carbamoylmethylsufinyl]ethyl 1-(4-chlorobenzoyl)-5-methoxy-2-methyl-3-indolylacetate 1-methyl-2-[N-[3-[3-(1-pyrrolidinylmethyl)phenoxy]propyl]carbamoylmethylsulfinyl]ethyl 1-(4-chlorobenzoyl)-5-methoxy-2-methyl-3-indolylacetate 1-methyl-2-[N-[3-[3-(piperidinomethyl)phenoxy]propyl]carbamoylmethylsulfonyl]ethyl 1(4-chlorobenzoyl)-5-methoxy-2-methyl-3-indolylacetate 1-methyl-2-[N-[3-[3-(1-pyrrolidinylmethyl)phenoxy]propyl]carbamoylmethylsulfonyl]ethyl 1-(4-chlorobenzoyl)-5-methoxy-2-methyl-3-indolylacetate 1-methyl-2-[N-[3-[3-(3-hydroxy-1-pyrrolidinylmethyl)phenoxy]propyl]carbamoylmethylsulfonyl]ethyl 1-(4-chlorobenzoyl)-5-methoxy-2-methyl-3-indolylacetate 3-[N-[3-[3-(piperidinomethyl)phenoxy]propyl]carbamoylmethylthio]propyl 1-(4-chlorobenzoyl)-5-methoxy-2-methyl-3-indolylacetate 3-[N-[3-[3-(1-pyrrolidinylmethyl)phenoxy]propyl]carbamoylmethylthio]propyl 1-(4-chlorobenzoyl)-5-methoxy-2-methyl-3-indolylacetate 3-[N-[3-[3-(piperidinomethyl)phenoxy]propyl]carbamoylmethylsulfinyl]propyl 1-(4-chlorobenzoyl)-5-methoxy-2-methyl-3-indolylacetate 3-[N-[3-[3-(1-pyrrolidinylmethyl)phenoxy]propyl]carbamoylmethylsulfinyl]propyl 1-(4-chlorobenzoyl)-5-methoxy-2-methyl-3-indolylacetate 3-[N-[3-[3-(piperidinomethyl)phenoxy]propyl]carbamoylmethylsulfonyl]propyl 1-(4-chlorobenzoyl)-5-methoxy-2-methyl-3-indolylacetate 3-[N-[3-[3-(1-pyrrolidinylmethyl)phenoxy]propyl]carbamoylmethylsulfonyl]propyl 1-(4-chlorobenzoyl)-5-methoxy-2-methyl-3-indolylacetate 2-hydroxy-3-[N-[3-[3-(piperidinomethyl)phenoxy]propyl]carbamoylmethylthio]propyl 1-(4-chlorobenzoyl)-5-methoxy-2methyl-3-indolylacetate 2-hydroxy-3-[N-[3-[3-(1-pyrrolidinylmethyl)phenoxy]propyl]carbamoylmethylthio]propyl 1-(4-chlorobenzoyl)-5-methoxy-2-methyl-3-indolylacetate 2-hydroxy-3-[N-[3-[3-(piperidinomethyl)phenoxy]propyl]carbamoylmethylsulfinyl]propyl 1-(4-chlorobenzoyl)-5-methoxy-2-methyl-3-indolylacetate 2-hydroxy-3-[N-[3-[3-(1-pyrrolidinylmethyl)phenoxy]propyl]carbamoylmethylsulfinyl]propyl 1-(4-chlorobenzoyl)-5-methoxy-2-methyl-3-indolylacetate 2-hydroxy-3-[N-[3-[3-(piperidinomethyl)phenoxy]propyl]carbamoylmethylsulfonyl]propyl 1-(4-chlorobenzoyl)-5-methoxy-2-methyl-3-indolylacetate 2-hydroxy-3-[N-[3-[3-(1-pyrrolidinylmethyl)phenoxy]propyl]carbamoylmethylsulfonyl]propyl 1-(4-chlorobenzoyl)-5-methoxy-2-methyl-3-indolylacetate For example, the compounds of the present invention can be produced by the following method:

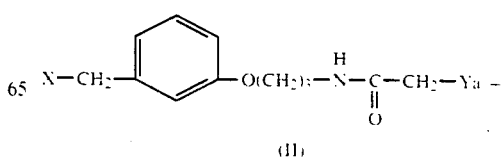

(II)

-continued

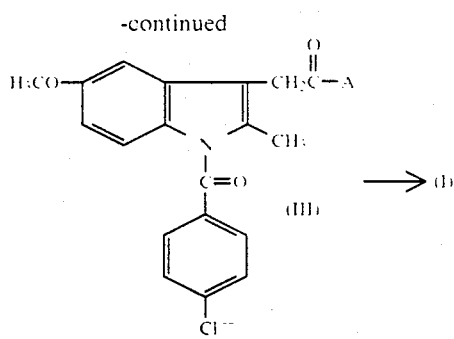

[wherein Ya denotes a hydroxyl group, a halogen atom,

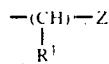

(wherein Z denotes a hydroxyl group or a halogen atom. R¹ and 1 each denote the same as that described above) or

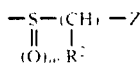

(wherein R², m. n and Z each denote the same as that described above). A denotes a hydroxyl group, a halogen atom or an active ester residue, and X denotes the same as that described above].

Namely, an acetamide compound expressed by the formula (II) is reacted with an indoleacetic acid derivative expressed by the formula (III) to form a compound (I) of the present invention.

Examples of indole derivatives (III) include acid halides, acid anhydrides, mixed acid anhydrides, 4-nitrophenyl esters and 2.4-dinitrophenyl esters.

The reaction is preferably effected at −5° to 150° C. in the presence or absence of a deoxidizer in a single or mixed reaction solvent selected from the group consisting of ether, tetrahydrofuran, dioxane, benzene, toluene, chloroform, dichloromethane, acetonitrile and dimethylformamide.

A tertiary amine such as pyridine, trimethylamine, triethylamine or the like, an alkali carbonate, alkali hydroxide, alkali hydride or basic resin can be appropriately selected and used as a deoxidizer.

When A in the formula (III) is a hydroxyl group, it is preferable to use a condensing agent such as 1,3-dicyclohexylcarbodiimide (DCC), 1.1'-carbonyldiimidazole (CDI) or the like.

An acetamide compound (II) which is a raw material in the above-described method can be produced by, for example, the following reaction:

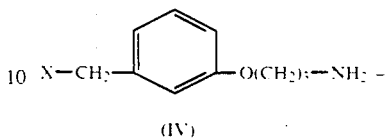

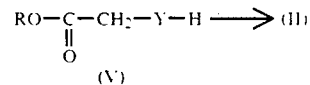

[wherein R denotes a lower alkyl group or a phenyl group which may be substituted, and X and Y each denote the same as that described above].

In other words, a phenoxypropylamine compound (IV) is reacted with an acetate compound (V) in a reaction solvent to form an acetamide compound (II). As occasion demands, the hydroxyl group of the compound (II) is then halogenated by a usual halogenation method to form a compound (II) in which Ya is a halogen atom.

The thus-formed compound (I) of the present invention can be changed to a desired salt by a general method.

A description will now be given on the pharmacological action, adverse effects and toxicity of the compounds (I) of the present invention.

(A) PHARMACOLOGICAL ACTION

Test of Carrageenin Plantar Edema

Male Wistar rats each having a body weight of about 100 to 200 g were divided into groups each consisting of 10 rats, and were fasted under water feeding for 24 hours. After the body weight of each rat had been measured, the volume of the right hind-leg of the rat was measured by using an apparatus for measuring plantar volumes. The rats were then divided into groups so that the groups have the same body weight average and plantar volume average. A test compound was suspended in an aqueous solution of 5% tragacanth gum and then orally administered to each of the rats. 0.1 ml of a physiological saline of 1% carrageenin was hypodarmically injected into the sole of the right hind-leg of each rat. The volume was measured for each rat every 1 hour for 5 hours. An edema rate was determined by using a rate of increase in the volume measured after treatment to the volume measured before treatment. The results are shown in Table 1.

TABLE 1

| Compound | Molecular weight | Dose | | Carrageenin edema Inhibition (%) rate at peak | $ED_{50}$ | |
|---|---|---|---|---|---|---|
| | | μmol/kg | mg/kg | | μmol/kg | mg/kg |
| Example 2 | 762.24 | 8.4 | 6.4 | 34.9 | 27.8 | 21.1 |
| | | 25.2 | 19.2 | 50.4 | | |
| | | 84.0 | 64.0 | 62.6 | | |
| Example 5 | 822.36 | 8.4 | 6.9 | 19.1 | 47.8 | 39.3 |
| | | 28.0 | 23.0 | 41.2 | | |
| | | 84.0 | 69.0 | 68.4 | | |
| | | 280.0 | 230.0 | 72.7 | | |
| Indomethacin | 357.81 | 2.8 | 1.0 | 24.6 | 20.6 | 7.4 |
| | | 8.4 | 3.0 | 49.8 | | |

TABLE 1-continued

| | | | | Carrageenin edema | | |
|---|---|---|---|---|---|---|
| | Molecular | Dose | | Inhibition (%) | ED$_{50}$ | |
| Compound | weight | μmol/kg | mg/kg | rate at peak | μmol/kg | mg/kg |
| (Control compound) | | 28.0 | 10.0 | 59.4 | | |
| | | 84.0 | 30.0 | 55.9 | | |

As seen from Table 1, the compounds in Examples 2 and 5 showed ED$_{50}$ values which were substantially the same as and about 2 times, respectively, that of indomethacin. Concerning the inhibition rate at the peak during administration of 84.0 μmol/kg, both compounds exhibited slightly higher values than that of indomethacin.

Test of Injury to Gastric Mucosa

Male Wistar rats each having a body weight of about 180 to 200 g were divided into groups consisting of 10 rats and were fasted for 24 hours. After body weight of each rat has been measured, a test compound was suspended in an aqueous solution of 5% tragacanth gum and then orally administered to each rat. The rats were fasted again, and after 5 hours had passed, they were killed by cervical dislocation. A 1% formalin solution was injected into the gastric cavity of each of the rats so that it was semifixed. The gaster of each rat was cut along the greater curvature of the stomach, and the ulcer index of each rat was measured under a stereoscopic microscope and determined by the Munchow method. The Mann-Whitney U-test was applied to the statistic data processing. The results are shown in Table 2.

TABLE 2

| Compound | Molecular weight | Dose | | Ulcer Index | Ulcer occurrence (%) |
|---|---|---|---|---|---|
| | | μmol/kg | mg/kg | | |
| Control | — | — | — | 0.0 ± 0.00 | 0 |
| Example 2 | 762.24 | 25.2 | 19.2 | 1.3 ± 0.63 | 0 |
| | | 84.0 | 64.0 | 5.9 ± 4.92 | 14 |
| | | 251.9 | 192.0 | 17.5 ± 15.84* | 40 |
| Example 5 | 822.36 | 28.0 | 23.0 | 0.1 ± 0.01 | 0 |
| | | 84.0 | 69.0 | 0.0 ± 0.00 | 0 |
| | | 280.0 | 230.0 | 0.0 ± 0.00 | 0 |
| Indomethacin (control compound) | 357.81 | 28.0 | 10.0 | 46.5 ± 15.00** | 70 |
| | | 56.0 | 20.0 | 52.8 ± 17.47** | 70 |
| | | 84.0 | 30.0 | 62.1 ± 16.50** | 80 |

*p < 0.05
**p < 0.01

As can be seen from Table 2, compounds of Examples 2 and 5 show an extremely low degree of injury to the gastric mucosa, as compared with indomethacin. Particularly, indomethacin shows 70% ulcer occurrence while the compound of Example 5 shows no occurrence of ulcer even when a dose by mole was 10 times that of indomethacin.

Test of Inhibition of Gastric-Acid Secretion by Histamine Stimulation

Male SD rats (Japan Charles River Co., Ltd.) each weighing 180 to 200 g were fasted for 24 hours before celiotomy with etherrization. A feeding tube (fr. 3.5) for injecting test medicines was inserted into the duodenum, and the pylorus was ligatured. A polyethylene tube (inner diameter: 7 mm) was used in the anterior stomach and gastric fistula was performed. After washing the inside of the stomach with heated physiological salt solution (37° C.) several times, the body was closed. A tube with a fin was inserted into the caudal vein and was fastened with a tape and it was connected to an infusion pump (Harvard). The rats were enclosed in a KN Ballman II cage (Natsume Seisakusho). Gastric juice flowed from the fistula was collected with a mess-cylinder every one hour. Starting from one hour after the operation, histamine was continuously injected at a rate of 1.4 ml/hour through the caudal vein. Then, test compounds suspended in 0.5% sodium caboxy methyl cellulose (Na-CMC) were administered one hour after the start of the histamine injection. The gastric juice thus extracted in a period from one hour after the administration of the chemical to four hours after that was titrated by using an automatic titration apparatus (Kyoto Electronic) with 0.1N NaOH to adjust pH 7, and the quantity of the gastric juice was measured to obtain the total acid output.

The inhibition rate (%) of the gastric acid secretion was calculated from the following equation, which results are shown in Table 1.

$$\text{Inhibition Rate (\%) of Gastric Acid secretion} = 1 - \frac{\text{total acid output of test compound group}}{\text{total acid output of control group}}$$

TABLE 3

| Test compound | Dose (mg/kg) | Gastric-acid secretion inhibition rate (%) |
|---|---|---|
| Example 5 | 22 | 47.4 |
| Example 5 | 44 | 74.1 |
| Cimetidine (Control compound) | 30 | 32.3 |

Acute Toxicity Test

A test compound was suspended in an aqueous solution of 5% gum arabic and then orally administered to each of 4 to 5-week old ICR male mice (Charles River Co., Ltd.) each having a body weight of 22 to 30 g in each group consisting of 3 to 4 mice, once in each of doses 25, 50, 75, 200 and 500 mg/kg. They were observed for 1 week.

As a result, all the mice in the groups, to which 25, 50 and 75 mg/kg of indomethacin were respectively administered, died within 48 to 96 hours. Meanwhile, death example was observed in all the groups, to which the compounds of Examples 2 and 5 were respectively administered, 1 week after the administration. As described above, each of the compounds of the present invention has an extremely low degree of toxicity as compared with indomethacin.

Each of the compounds of the present invention is administered in an oral, intramuscular, subcutaneous, or intravenous manner or a parenteral manner used for suppositories. Although the dose of each compound depends upon the disease conditions, age and sexuality of a patient, it is generally 1 to 1000 mg per day for one adult, and it is particularly preferable to administer 5 to 300 mg of a compound 1 to 3 times a day.

The compounds of the present invention are formed into preparations such as tablets, granules, powder medicines, capsules, injection drugs, solutions, eye drops, nasal drops, suppositories, ointments, plasters, cream drugs, suspensions, aqueous liniments, or the like by normal methods used in the technical field of preparation. Examples of additives that are used in preparation include cellulose, lactose, sucrose, mannitol, sorbitol, starch (potato, cone, rice, wheat and the like), gelatin, tragacanth rubber, polyvinyl pyrrolidone, carboxymethyl cellulose, sodium carboxymethyl cellulose, calcium carboxymethyl cellulose, hydroxypropyl cellulose, talc, magnesium stearate, calcium stearate, synthetic aluminum silicate, polyethylene glycol, polyoxyethylene hardened castor oil, polysorbate, propylene glycol, glycerin, boric acid, benzalconium chloride, chlorobutanol, sodium dehydroacetate, wittepsole, macrogol, cacao butter, sodium chloride, potassium chloride, alcohol, water and the like. Some of these additives are appropriately selected and used.

EXAMPLES

The present invention is described in detail below with reference to examples.

EXAMPLE 1

N-[3-[3-(piperidinomethyl)phenoxy]propyl]carbamoyl-methyl 1-(4-chlorobenzoyl)-5-methoxy-2-methyl-3-indolylacetate

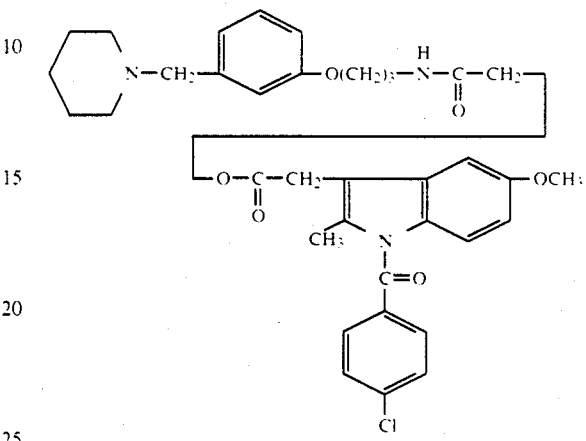

3.6 g of 2-hydroxy-N-[3-[3-(piperidinomethyl)-phenoxy]propyl] acetamide and 1.5 ml of pyridine were dissolved in 50 ml of dry acetonitrile, and 4 g of 1-(4-chlorobenzoyl)-5-methoxy-2-methyl-3-indolylacetyl chloride was gradually added to the resultant solution at room temperature under agitation over a time of 20 minutes. After agitation at room temperature for 1 hour, the solvent was distilled off under reduced pressure to obtain an oily substance. 30 ml of a saturated aqueous solution of sodium hydrogencarbonate was then added to the oily substance, followed by 3 extractions with 50 ml of chloroform. After the thus-obtained extract had been then dried over anhydrous sodium sulfate, chloroform was distilled off under reduced pressure. The thus-obtained residue was purified by using silica gel column chromatography (developing solvent; chloroform:methanol=20:1) to obtain as an oily substance 6.4 g of N-[3-[3-(piperidinomethyl)phenoxy]propyl]carbamoyl-methyl 1-(4-chlorobenzoyl)-5-methoxy-2-methyl-3-indolylacetate.

NMR (CDCl$_3$) δ: 1.33-1.67 (6H, br), 1.76 (2H, q), 2.20-2.50 (4H, br), 2.36 (3H, s), 3.25 (2H, s), 3.38 (2H, s), 3.72 (2H, s), 3.79 (3H, s), 3.88 (2H, t), 4.55 (2H, s), 6.13 (1H, br), 6.66-7.25 (7H, m), 7.38 (2H, d), 7.60 (2H, d)

EXAMPLE 2

N-[3-[3-(piperidinomethyl)phenoxy]propyl]carbamoyl-methyl 1-(4-chlorobenzoyl)-5-methoxy-2-methyl-3-indolylacetate maleate 6.4 g of the indoleacetic acid compound obtained in Example 1 was dissolved in 50 ml of benzene, and a solution obtained by dissolving 1.4 g of maleic acid in 50 ml of ether was added to the resultant solution. After excess ether had been further added to the resultant mixture and then cooled, the solvent layer was removed by decantation. 50 ml of benzene was then added to the oily residue, followed by agitation under cooling, to obtain 6.5 g of slightly yellow crystals. The thus-obtained crystals were recrystallized from benzene to obtain N-[3-[3-(piperidinomethyl)phenoxy]propyl]carbamoylmethyl 1-(4-chlorobenzoyl)-5-methoxy-2-methyl-3-indolylacetate maleate.

Melting point: 92° to 95° C.

IR (KBr) cm$^{-1}$: 3400–3800, 2940, 1745, 1663, 1580, 1480, 1360, 1165.

NMR (CDCl$_3$) δ: 1.5–2.1 (8H, br), 2.30 (3H, s), 3.0–3.7 (6H, br), 3.76 (3H, s), 3.7–4.1 (2H, m), 4.05 (2H, br), 4.55 (2H, s), 6.26 (2H, s), 6.50–7.26 (7H, m), 7.36 (2H, d), 7.58 (2H, d), 13.5–14.7 (2H, br).

EXAMPLE 3

N-[3-[3-(piperidinomethyl)phenoxy]propyl]carbamoylmethyl 1-(4-chlorobenzoyl)-5-methoxy-2-methyl-3-indolylacetate maleate 366 mg of sodium hydride (55%) was suspended in 6 ml of anhydrous dimethylformamide, and 3 g of indomethacin was added to the resultant suspension under agitation. 2 g of potassium iodide and 2.6 g of N-[3-[3-piperidinomethyl)phenoxy]propyl]-2-chloroacetamide were added to the resultant mixture, and the mixture was then heated at 80° to 90° C. for 3 hours under agitation. The solvent was distilled off under reduced pressure, and the resultant residue was dissolved in 80 ml of water. The resultant aqueous solution was then subjected to 2 extractions with 60 ml of ethyl acetate. The obtained organic solvent layer was washed with a saturated salt solution and then dried over magnesium sulfate. The solvent was distilled off under reduced pressure, and the resultant residue was purified by separation using silica gel column chromatography (developing solvent: chloroform:methanol=97:3) to obtain 1.4 g of an oily substance.

The thus-obtained oily substance was dissolved in 20 ml of benzene, and an saturated ether solution of maleic acid was then added to the resultant solution until oily precipitates were no longer produced. After the solvent layer had been then removed by decantation, 20 ml of benzene was added to the thus-obtained oily substance, followed by agitation under cooling, to obtain 1.6 g slightly yellow crystals of N-[3-[3-(piperidinomethyl)phenoxy]propyl]carbamoylmethyl 1-(4-chlorobenzoyl)-5-methoxy-2-methyl-3-indolylacetate maleate.

Melting point: 92°–95° C.

EXAMPLE 4

2-[N-[3-[3-(piperidinomethyl)phenoxy]propyl]carbamoylmethylthio]ethyl 1-(4-chlorobenzoyl)-5-methoxy-2-methyl-3-indolylacetate

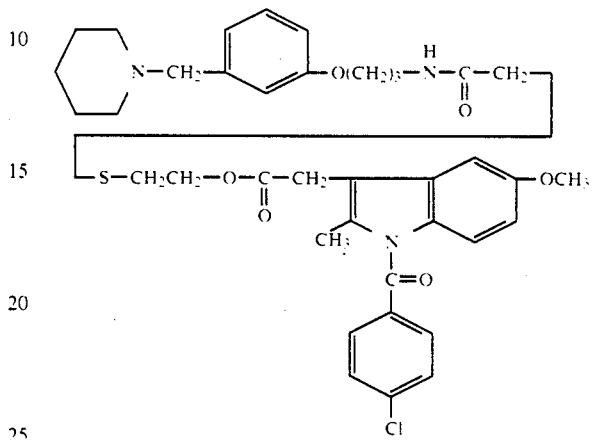

4.2 g of 2-(2-hydroxyethyl-1-thio)-N-[3-[3-(piperidinomethyl)phenoxy]propyl] acetamide and 5 ml of anhydrous pyridine were dissolved in 70 ml of dry acetonitrile, and 4.8 g of 1-(4-chlorobenzoyl)-5-methoxy-2-methyl-3-indolylacetyl chloride was gradually added to the resultant solution over a time of 20 minutes under agitation at room temperature. The resultant mixture was then agitated for 1 hour at the same temperature and further at 40° to 50° C. for 1 hour. The solvent was distilled off under reduced pressure, and 50 ml of a saturated aqueous solution of sodium hydrogencarbonate was then added to the resultant residue. The resultant mixture was then subjected to 2 extractions with 50 ml and 30 ml of chloroform, and the chloroform solution was dried over anhydrous sodium sulfate. After the solvent had been distilled off under reduced pressure, the resultant residue was purified by silica gel column chromatography (developing solvent: chloroform:methanol=42:3) to obtain as an oily substance 7.2 g of 2-[N-[3-[3-(piperidinomethyl)phenoxy]propyl]carbamoylmethylthio]ethyl 1-(4-chlorobenzoyl)-5-methoxy-2-methyl-3-indolylacetate.

IR (liquid film) cm$^{-1}$: 3500–3400, 2950, 1730, 1655, 1590, 1530, 1488, 1452, 1262, 1220, 1160, 1103, 1038, 752.

NMR (CDCl$_3$) δ:1.50 (6H, br), 1.99 (2H, q), 2.35 (3H, s), 2.25–2.55 (4H, br), 2.79 (2H, t), 3.20 (2H, s), 3.41 (2H, t), 3.45 (2H, s), 3.67 (2H, br), 3.81 (3H, s), 4.02 (2H, t), 4.28 (2H, t), 6.52–7.25 (7H, m), 7.42 (2H, d), 7.67 (2H, d).

The thus-obtained oily substance was dissolved in isopropyl ether and then crystallized by being allowed to stand at 5° C. for 12 hours.

Melting point: 81°–83° C.

IR (KBr) cm$^{-1}$: 3300, 1730, 1679, 1640.

NMR (CDCl$_3$) δ:1.34–1.48 (2H, m), 1.48–1.62 (4H, m), 1.99 (2H, m), 2.24–2.42 (4H, m), 2.37 (3H, s), 2.77 (2H, t), 3.21 (2H, s), 3.42 (2H, s), 3.48 (2H, q), 3.67 (2H, s), 3.83 (3H, s), 4.04 (2H, t), 4.26 (2H, t), 6.64–7.22 (8H, m), 7.46 (2H, d), 7.66 (2H, d).

| Elementary analysis value (as C₃₈H₄₄N₃O₆SCl): | | |
|---|---|---|
| | C | H | N |
| Experimental value | 64.70 | 6.36 | 5.81 |
| Calculated value | 64.62 | 6.28 | 5.95 |

EXAMPLE 5

2-[N-[3-[3-(piperidinomethyl)phenoxy]propyl]carbomoylmethylthio]ethyl 1-(4-chlorobenzoyl)-5-methoxy-2-methyl-3-indolylacetate maleate The same procedure as in Example 2 was followed with the exception that 6 g of the indoleacetic acid compound obtained in Example 4 was used to obtain as an amorphous substance 6.5 g of 2-[N-[3-[3-(piperidinomethyl)phenoxy]propyl]carbamoylmethylthio]ethyl 1-(4-chlorobenzoyl)-5-methoxy-2-methyl-3-indolylacetate maleate.

NMR (CDCl₃) δ:1.53–2.25 (8H, br), 2.33 (3H, s), 2.82 (2H, t), 3.21 (2H, s), 3.33–3.70 (6H, m), 3.67 (2H, s), 3.80 (3H, s), 3.99 (2H, t), 4.26 (2H, t), 6.30 (2H, s), 6.65–7.30 (7H, m), 7.37 (2H, d), 7.63 (2H, d), 12.6–13.2 (2H, br).

EXAMPLE 6

6.5 g of the indoleacetic acid compound obtained in Example 4 was dissolved in 20 ml of acetonitrile, and a solution obtained by dissolving 1.3 g of oxalic acid dihydrate in 80 ml of acetonitrile was then added to the resultant solution. After the resultant mixture had been allowed to stand at room temperature for 5 hours and then at 4° C. for 20 hours, the crystals separated were filtered off and then recrystallized from acetonitrile to obtain 5.5 g of 2-[N-[3-[3-(piperidinomethyl)phenoxy]-propyl]carbamolymethylthio]ethyl 1-(4-chlorobenzoyl)-3-methoxy-2-methyl-3-indolylacetate oxalate.

Melting point: 102°–103° C.

IR (KBr) cm⁻¹: 3290, 2600–2200, 1735, 1675, 600.

NMR (CDCl₃) δ:1.35 (2H, m), 1.83 (4H, m), 1.98 (2H, m), 2.36 (3H, s), 2.58 (2H, br), 2.82 (2H, t), 3.25 (2H, s), 3.44 (2H, m), 3.59 (2H, br), 3.68 (2H, s), 3.83 (3H, s), 3.98 (2H, t), 4.12 (2H, s), 4.28 (2H, t), 6.64–7.48 (8H, m), 7.47 (2H, d), 7.66 (2H, d).

| Elementary analysis value (as C₃₈H₄₄N₃O₆SCl·C₂H₄O₄·2H₂O) | | | |
|---|---|---|---|
| | C | H | N |
| Experimental value | 64.70 | 6.36 | 5.81 |
| Calculated value | 64.62 | 6.28 | 5.95 |

EXAMPLE 7

2-[N-[3-[3-(1-pyrrolidinylmethyl)phenoxy]propyl]carbamoylmethylthio]ethyl 1-(4-chlorobenzoyl)-5-methoxy-2-methyl-3-indolylacetate

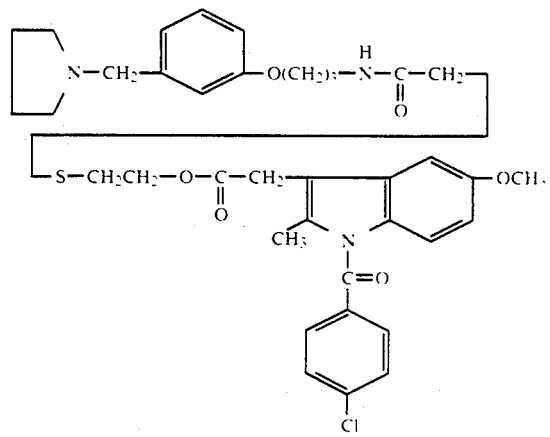

530 mg of N-[3-[3-(1-pyrrolidinylmethyl)phenoxy]-propyl]-2-(2-hydroxyethyl-1-thio) acetamide was dissolved in a mixture solvent containing 7 ml of dry acetonitrile and 0.5 ml of pyridine, and 775 mg of 1-(4-chlorobenzoyl)-5-methoxy-2-methyl-3-indolylacetyl chloride was then added to the resultant solution at a stroke under ice-cooling. After addition, the resultant mixture was agitated for 10 minutes in an iced bath, 30 minutes at room temperature, and then for 1 hour at 50° to 60° C., and the reaction solution was then concentrated under reduced pressure. 16 ml of a saturated aqueous solution of sodium hydrogencarbonate was poured on the thus-obtained residue, followed by extraction with chloroform. The extract was dried over magnesium sulfate, and chloroform was then distilled off under reduced pressure to obtain a brown oily brown substance. The thus-obtained oily substance was subjected to silica gel column chromatography (developing solvent: chloroform: methanol=6:1) to obtain as a slightly yellow oily substance 332 mg of 2-[N-[3-[3-(1-pyrrolidinylmethyl)phenoxy]propyl]carbamolymethylthio]ethyl 1-(4-chlorobenzoyl)-5-methoxy-2-methyl-3-indolylacetate.

IR (liquid film) cm⁻¹: 1735, 1675.

NMR (CDCl₃) δ:1.60–2.20 (6H, m), 2.37 (3H, s), 2.40–3.10 (6H, m), 3.22 (2H, s), 3.25–4.45 (10H, m), 3.85 (3H, s), 6.60–7.80 (12H, m).

EXAMPLE 8

2-[N-[3-[3-(1-pyrrolidinylmethyl)phenoxy]propyl]carbomoylmethylsulfonyl]ethyl 1-(4-chlorobenzoyl)-5-methoxy-2-methyl-3-indolylacetate

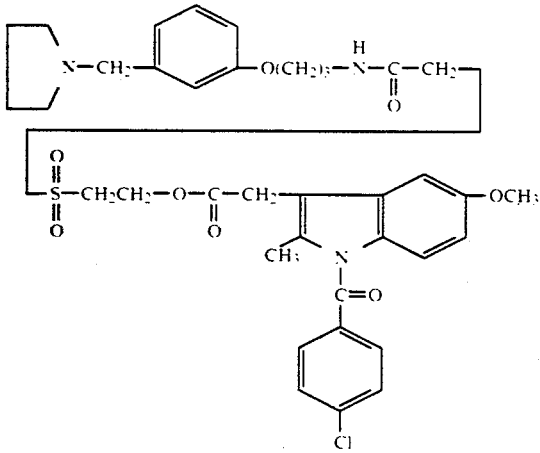

(a) 1.3 g of N-[3-[3-(1-pyrrolidinylmethyl)phenoxy]propyl-2-(2-hydroxyethyl-1-thio) acetamide was dissolved in 8 ml of acetic acid, and 9.1 g of an aqueous solution of 31% hydrogen peroxide was then added to the resultant solution, followed by agitation under heating at an external temperature of 65° C. After 1.5 hours had passed, 10 ml of water was added to the mixture which was then concentrated under reduced pressure. 16 ml of a saturated aqueous solution of sodium hydrogencarbonate was then added to the remaining solution, and the resultant mixture was then subjected to extraction with chloroform. After the extract had been dried over magnesium sulfate, chloroform was distilled off under reduced pressure to obtain a brown oily substance. The thus-obtained substance was then subjected to silica gel column chromatography (developing solvent:chloroform:methanol=4:1) to obtain as a colorless oily substance 377 mg of N-[3-[3-(1-pyrrolidinylmethyl)phenoxy]propyl]-2-(2-hydroxyethyl-1-sulfonyl) acetamide.

IR (liquid film) cm$^{-1}$: 3300, 1650, 1310, 1115.

NMR (CDCl$_3$) δ:1.75-2.30 (6H, m), 2.65-3.25 (4H, m), 3.25-3.70 (m), 3.80-4.50 (m), 6.65-7.75 (5H, m).

(b) 370 mg of N-[3-[3-(1-pyrrolidinymethyl)phenoxy]propyl]-2-(2-hydroxyethyl-1-sulfonyl) acetamide was dissolved in a solvent containing 5 ml of dry acetonitrile and 0.3 ml of pyridine, and 966 mg of 1-(4-chlorobenzoyl)-5-methoxy-2-methyl-3-indolylacetyl chloride was then added to the resultant solution at room temperature, followed by agitation at an external temperature of 50° C. After 1.5 hours had passed, the reaction solution was poured into a mixture containing 20 ml of a saturated aqueous solution of sodium hydrogencarbonate and 20 ml of a saturated aqueous solution of sodium chloride. After extraction with chloroform, the extract was dried over magnesium sulfate, and chloroform was then distilled off under reduced pressure to obtain a brown oily substance. The thus-obtained residue was subjected to silica gel column chromatography (developing solvent:chloroform:methanol=7:1) to obtain a yellow oily substance. The thus-obtained yellow oily substance was then subjected to alumina column chromatography (developing solvent: chloroform:methanol=7:1) to obtain as a yellow oily substance 401 mg of 2-[N-[3-[3-(1-pyrrolidinylmethyl)phenoxy]propyl]carbamoylmethylsulfonyl]ethyl 1-(4-chlorobenzoyl)-5-methoxy-2-methyl-3-indolylacetate.

IR (KBr) cm$^{-1}$: 1735, 1670, 1320, 1150-1110.

NMR (CDCl$_3$) δ:1.55-2.15 (6H, m), 2.25-2.75 (4H, m), 2.35 (3H, s), 3.15-4.20 (15H, m), 4.55 (2H, t), 6.50-7.80 (12H, m).

EXAMPLE 9

2-[N-[3-[3-(1-pyrrolidinylmethyl)phenoxy]propyl]carbamoylmethylsulfinyl]ethyl 1-(4-chlorobenzoyl)-5-methoxy-2-methyl-3-indolylacetate

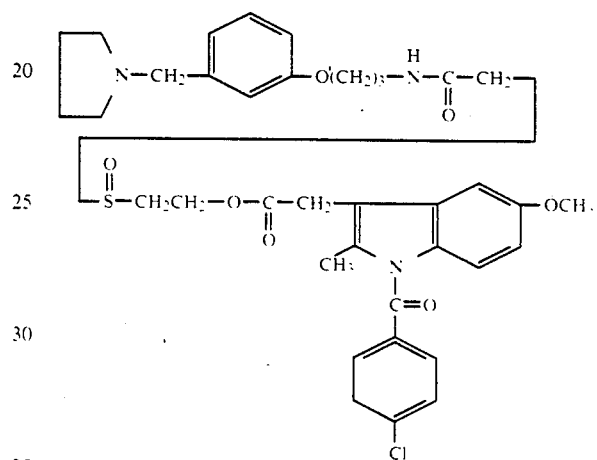

(a) 918 mg of N-[3-[3-(1-pyrrolidinylmethyl)phenoxy]propyl]-2-(2-hydroxyethyl-1-thio) acetamide was dissolved in 3 ml of acetic acid, and 549 mg of an aqueous solution of 31% hydrogen peroxide was then dropwisely added to the resultant solution at room temperature, followed by agitation at the same temperature. After 1.5 hours had passed, the resultant mixture was poured into a saturated aqueous solution of sodium hydrogencarbonate, and sodium chloride was then added to the mixture to saturate it. After extraction with butanol, the extract was dried over magnesium sulfate, and n-butanol was then distilled off under reduced pressure to obtain 804 mg of a slightly brown oily substance. The thus-obtained oily substance was then subjected to alumina column chromatography (developing solvent:chloroform:methanol=7:1) to obtain as an oily substance of N-[3-[3-(1-pyrrolidinylmethyl)phenoxy]propyl]2-(2-hydroxyethyl-1-sulfinyl) acetamide.

IR (liquid film) cm$^{-1}$: 3275, 1650, 1025.

NMR (CDCl$_3$) δ:1.60-2.20 (6H, m), 2.30-2.75 (4H, m), 3.03 (2H, t), 3.20-4.25 (11H, m), 6.65-7.65 (5H, m).

(b) 637 mg of N-[3-[3-(1-pyrrolidinylmethyl)phenoxy]propyl]-2-(2-hydroxyethyl-1-sulfinyl) acetamide was dissolved in a mixture containing 7 ml of acetonitrile and 1 ml of pyridine, and 1.3 g of 1-(4-chlorobenzoyl)-5-methoxy-2-methyl-3-indolylacetyl chloride was then added to the resultant solution at room temperature, followed by agitation at an external temperature of 50° C. After 1 hour had passed, the reaction solution was concentrated under reduced pressure, and 15 ml of a saturated aqueous solution of sodium hydrogencarbonate was poured on the concentrated solution. The resulting solution was then subjected to extraction with chloroform, and the extract was dried over magnesium sulfate. Chloroform was then distilled off under reduced pressure to obtain a brown oily substance. The thus-obtained oily substance was then subjected to alumina column chromatography (developing solvent: chloroform:methanol=7:1) to obtain 1.6 g of a brown oily substance. The thus-obtained oily substance was then subjected to silica gel column chromatography (developing solvent: chloroform:methanol=7:1) to obtain as a slightly yellow oily substance 280 mg of 2-[N-[3-[3-(1-pyrrolidinylmethyl)phenoxy]propyl]carbamoylmethylsulfinyl]ethyl 1-(4-chlorobenzoyl)-5-methoxy-2-methyl-3-indolylacetate.

IR (CHCl₃) cm⁻¹: 1730, 1665, 1030.

NMR (CDCl₃) δ:1.68–2.20 (6H, m), 2.38 (3H, s), 2.48–2.90 (4H, m), 2.90–4.28 (15H, m), 4.38–4.68 (2H, m), 6.70–7.88 (12H, m).

EXAMPLE 10

2-[N-[3-[3-(piperidinomethyl)phenoxy]propyl]carbamoylmethylsulfonyl]ethyl 1-(4-chlorobenzoyl)-5-methoxy-2-methyl-3-indolylacetate

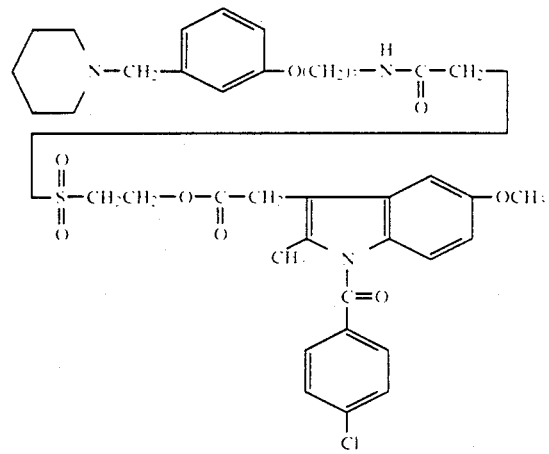

(a) The same procedure as in the method (a) in Example 8 was followed with the exception that N-[3-[3-(piperidinomethyl)phenoxy]propyl]-2-(2-hydroxyethyl-1-thio) acetamide was used to obtain N-[3-[3-(piperidinomethyl)phenoxy]propyl]-2-(2-hydroxyethyl-1-sulfonyl) acetamide.

(b) The same procedure as in Example 4 was performed with the exception that 477 mg of the acetamide compound obtained in (a), 540 mg of 1-(4-chlorobenzoyl)-5-methoxy-2-methyl-3-indolylacetyl chloride, 119 mg of anhydrous pyridine and 10 ml of dry acetonitrile were used to obtain as an oily substance 320 mg of 2-[N-[3-[3-(piperidinomethyl)phenoxy]propyl]carbamoylmethylsulfonyl]ethyl 1-(4-chlorobenzoyl)-5-methoxy-2-methyl-3-indolylacetate.

IR (liquid film) cm⁻¹: 1735, 1660, 1325.

NMR (CDCl₃) δ:1.34–1.79 (6H, m), 2.10–2.33 (2H, m), 2.48–2.94 (7H, m), 3.16–4.40 (17H, m), 6.43–7.75 (11H, m).

EXAMPLE 11

2-[N-[3-[3-(piperidinomethyl)phenoxy]propyl]carbamoylmethylsulfinyl]ethyl 1-(4-chlorobenzoyl)-5-methoxy-2-methyl-3-indolylacetate

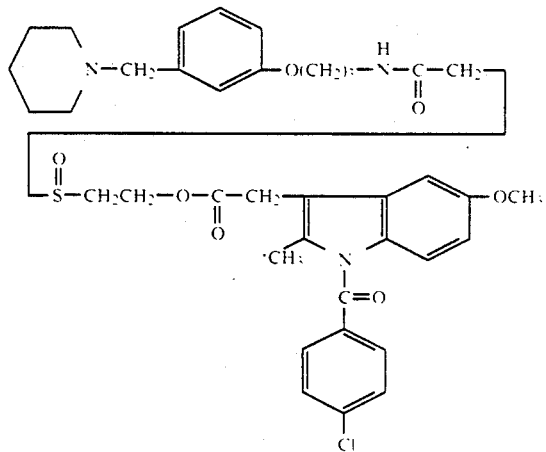

(a) The same procedure as in the method (a) in Example 8 was followed with the exception that N-[3-[3-(piperidinomethyl)phenoxy]propyl]-2-(2-hydroxyethyl-1-thio) acetamide was used to obtain N-[3-[3-(piperidinomethyl)phenoxy]propyl]-2-(2-hydroxyethyl-1-sulfinyl) acetamide.

(b) The same procedure as in Example 4 was followed with the exception that 262 mg of the acetamide compound obtained in (a), 309 mg of 1-(4-chlorobenzoyl)-5-methoxy-2-methyl-3-indolyacetyl chloride, 70 mg of anhydrous pyridine and 5 ml of dry acetonitrile were used to obtain as an oily substance 168 mg of 2-[N-[3-[3-(piperidinomethyl)phenoxy]propyl]carbamoylmethylsulfinyl]ethyl 1-(4-chlorobenzoyl)-5-methoxy-2-methyl-3-indolylacetate.

IR (CHCl₃) cm⁻¹: 1730, 1670, 1030.

NMR (CDCl₃) δ:1.37–1.74 (6H, m), 1.84–2.19 (2H, m), 2.19–2.55 (7H, m), 3.13 (2H, t), 3.30–4.21 (15H, m), 4.40–4.67 (2H, m), 6.65–7.84 (11H, m).

Drug preparation examples according to the invention will be described below.

TABLET 100 g of the compound of Example 5, 126 g of lactose, 12 g of calcium carboxymethyl cellulose and 2 g of magnesium stearate were mixed well and compression-molded by a tablet machine to form tablets.

GRANULE 25 g of the compound of Example 5 was dissolved in 170 ml of ethanol. 200 g of lactose, 250 g of cone starch and 25 g of hydroxypropyl cellulose were mixed in a high-speed mixer, and the resulting mixture was then added to the solution separately prepared and kneaded well. The thus-obtained kneaded material was granulated by an extrusion granulating machine and then air-dried at 40° C. for 2 hours to form granules.

CAPSULE 100 g of the compound of Example 2, 192 g of lactose and 6 g of hydroxypropyl cellulose were well mixed, and 2 g of talc was added to the thus-obtained mixture. The mixture was then charged in each capsule to form a capsule medicine.

INJECTION 10 g of the compound of Example 5 was dissolved in polysorvate 80, and the thus-obtained solution and 8 g of sodium chloride were dissolved in distilled water used for injection so that the total volume was 1 l. The thus-formed solution was filtered and sterilized and then charged in 1-ml ampoules to form injections.

SUPPOSITORY 100 g of the compound of Example 7 was dissolved in 1900 g of Wittepsole, and the resultant solution was then charged in a suppository container and then cooled to form suppositories.

EYE DROPS 0.3 g of the compound of Example 5, 0.4 g of chlorobutanol, 602.0 g of polyoxyethylene hardened castor oil and 0.2 ml of ethanol were agitated on a water bath at about 80° C. to form a solution. Purified water at about 80° C. was then added to the thus-formed solution. After dissolution had been confirmed, the resultant mixture was cooled, and 1.0 g of boric acid was added to the mixture. Purified water was added to the mixture so that the total volume was 100 ml, and an appropriate amount of borax was added to the resultant solution. After the pH value of the solution had been adjusted to 7.0, the solution was filtered by 0.22 μm membrane filter, charged in a 10-ml eye dropper, capped and then sterilized by heating to form eye drops.

INDUSTRIAL APPLICABILITY

Each of the compounds (I) of the present invention has an extremely reduced degree of adverse effects such as damage to the alimentary canal, which are great problems of conventional non-steroidal anti-flammatory drugs represented by indomethacin, a low degree of toxicity and an effect of inhibiting carrageenin edema to an extent which is substantially the same as indomethacin. The compounds also exhibit excellent anti-ulcer activities. They are therefore very useful as anti-inflammatory, anti-rheumatic and anti-ulcer drugs.

What is claimed is:
1. An indoleacetic acid compound expressed by the following formula (I):

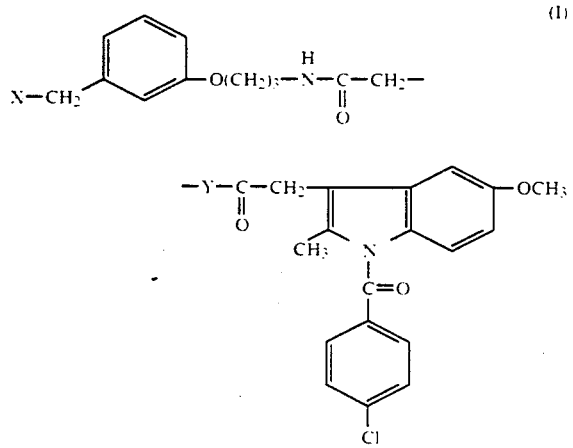

wherein X denotes a piperidino group, 1-pyrrolidinyl group or 3-hydroxy-1-pyrrolidinyl group; Y denotes

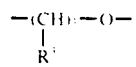

wherein $R^1$ denotes a hydrogen atom or a lower alkyl group, and l denotes a 0, 1 or 2 or

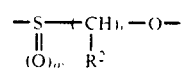

wherein $R^2$ denotes a hydrogen atom, a lower alkyl group or a hydroxyl group, m denotes 0, 1 or 2, and n denotes 1, 2 or 3, or a pharmaceutically acceptable salt thereof.

2. A method of preparing an indoleacetic acid compound as claimed in claim 1 comprising reacting an acetamide compound expressed by the following formula (II):

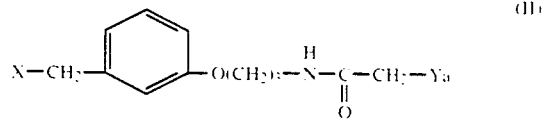

wherein X denotes a piperidino group, 1-pyrrolidinyl group or 3-hydroxy-1-pyrrolidinyl group; Ya denotes a hydroxyl group, a halogen atom,

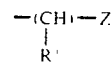

wherein $R^1$ denotes a hydrogen atom or a lower alkyl group; Z denotes a hydroxyl group or a halogen atom; and l is 0, 1 or 2 or

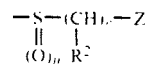

wherein $R^2$ denotes a hydrogen atom, a lower alkyl group or a hydroxyl group; m is 0, 1 or 2; n is 1, 2 or 3; and Z is the same as that described above and an indole compound expressed by the following formula (III):

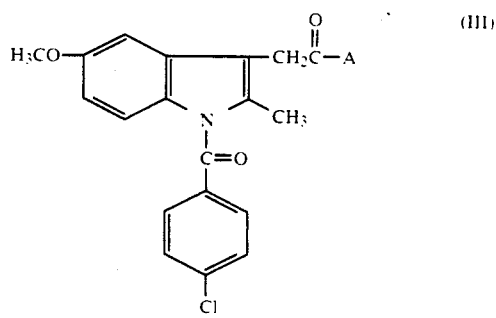

wherein A denotes a hydroxyl group, a halogen atom or an active ester residue.

3. An anti-inflammatory drug comprising as an active ingredient an effective amount of an indoleacetic acid compound as claimed in claim 1 and a pharmaceutical carrier.

4. An antirheumatic drug comprising as an active ingredient an effective amount of an indoleacetic acid compound as claimed in claim 1 and a pharmaceutical carrier.

5. An anti-ulcer drug comprising as an active ingredient an effective amount of an indoleacetic acid compound as claimed in claim 1 and a pharmaceutical carrier.

* * * * *